(12) United States Patent
Krumme

(10) Patent No.: US 8,808,729 B2
(45) Date of Patent: Aug. 19, 2014

(54) MULTILAYERED TRANSMUCOSAL THERAPEUTIC SYSTEM

(75) Inventor: Markus Krumme, Denville, NJ (US)

(73) Assignee: LTS Lohmann Therapie-Systeme AG, Andernach (DE)

( * ) Notice: Subject to any disclaimer, the term of this patent is extended or adjusted under 35 U.S.C. 154(b) by 2097 days.

(21) Appl. No.: 10/533,835

(22) PCT Filed: Nov. 4, 2003

(86) PCT No.: PCT/EP03/12272
§ 371 (c)(1), (2), (4) Date: May 4, 2005

(87) PCT Pub. No.: WO2004/043426
PCT Pub. Date: May 27, 2004

(65) Prior Publication Data
US 2006/0039957 A1 Feb. 23, 2006

(30) Foreign Application Priority Data
Nov. 13, 2002 (DE) .................................. 102 52 726

(51) Int. Cl.
*A61K 9/70* (2006.01)
*A61K 9/00* (2006.01)

(52) U.S. Cl.
CPC .............. *A61K 9/006* (2013.01); *A61K 9/7007* (2013.01)
USPC ....................................................... 424/443

(58) Field of Classification Search
None
See application file for complete search history.

(56) References Cited

U.S. PATENT DOCUMENTS

| 4,292,299 | A |   | 9/1981  | Suzuki et al.      |         |
|-----------|---|---|---------|--------------------|---------|
| 4,517,173 | A | * | 5/1985  | Kizawa et al.      | 424/435 |
| 4,615,697 | A |   | 10/1986 | Robinson           |         |
| 4,713,243 | A |   | 12/1987 | Schiraldi et al.   |         |
| 4,740,365 | A | * | 4/1988  | Yukimatsu et al.   | 424/435 |
| 4,772,470 | A |   | 9/1988  | Inoue et al.       |         |
| 4,855,142 | A |   | 8/1989  | Fankhauser et al.  |         |
| 4,876,092 | A |   | 10/1989 | Mizobuchi et al.   |         |
| 5,719,197 | A |   | 2/1998  | Kanios et al.      |         |
| 6,072,100 | A | * | 6/2000  | Mooney et al.      | 602/48  |
| 6,242,004 | B1| * | 6/2001  | Rault              | 424/472 |
| 6,375,963 | B1| * | 4/2002  | Repka et al.       | 424/402 |
| 6,780,504 | B2|   | 8/2004  | Rupprecht et al.   |         |
| 2002/0142036 | A1 | | 10/2002 | Rupprecht et al.   |         |

FOREIGN PATENT DOCUMENTS

| DE | 199 32 603   |   | 1/2001  |               |
|----|--------------|---|---------|---------------|
| EP | 0275550      |   | 7/1988  |               |
| WO | WO 98/17251  | * | 4/1998  | ............... A61K 9/00 |
| WO | WO 9955312   |   | 11/1999 |               |
| WO | WO 01/03917  | * | 1/2001  | .............. B32B 27/00 |

OTHER PUBLICATIONS

Cui, et al.; "Bilayer Films for Mucosal (Genetic) Immunization via the Buccal Route in Rabbits;" *Pharmaceutical Research* (New York); vol. 19, No. 7, Jul. 2002; pp. 947-953

Solomonidou, et al.; "Effect of Carbomer Concentration and Degree of Neutralization on the Mucoadhesive Properties of Polymer Films;" *Journal of Biomaterials Science Polymer Edition*; vol. 12, No. 11 (2001), pp. 1191-1205.

Cui, et al.; "Bilayer Films for Mucosal (Genetic) Immunization via the Buccal Route in Rabbits;" *Pharmaceutical Research*(New York); vol. 19, No. 7, Jul. 2002; pp. 947-953.

Solomonidou, et al.; "Effect of Carbomer Concentration and Degree of Neutralization on the Mucoadhesive Properties of Polymer Films;" *Journal of Biomaterials Science Polymer Edition;*vol. 12, No. 11 (2001), pp. 1191-1205.

* cited by examiner

*Primary Examiner* — Kevin S Orwig
*Assistant Examiner* — Ping Cao
(74) *Attorney, Agent, or Firm* — D. Peter Hochberg; Sean F. Mellino; Richard A. Wolf

(57) ABSTRACT

A film-shaped therapeutic system comprising at least two layers connected with each other, for transmucosal administration of active substances. The system has a layer which is mucoadhesive in an aqueous environment and a mono-layered or multi-layered backing layer. At least one of these layers contains an active substance. The mucoadhesive layer is capable of swelling in an aqueous media, but is insoluble or only poorly soluble in an aqueous media.

41 Claims, 1 Drawing Sheet

MULTILAYERED TRANSMUCOSAL THERAPEUTIC SYSTEM

BACKGROUND OF INVENTION

Cross-Reference to Related Application

This application is a National Stage application of International Application No. PCT/EP03/012272, filed on Nov. 4, 2003, which claims priority of German application number 102 52 726.1, filed on Nov. 13, 2002.

FIELD OF THE INVENTION

The invention relates to a multilayered film-shaped therapeutic system for transmucosal administration of active substances, especially of medicinal substances. These systems are suitable for rapid delivery of active substances over a prolonged period in a controlled manner.

DESCRIPTION OF THE PRIOR ART

Mucoadhesive medicament forms are known in the state of the art for example in the form of mucoadhesive tablets, disks or film-shaped administration forms. Some of those medicament forms are already available on the market. Mucoadhesive medicament forms are applied to the mucosa, especially to the oral mucosa (buccal and/or gingival mucosa), thereby enabling the delivery of the active substance contained therein and absorption via the mucosa. It is advantageous here that the active substances enter the circulation quickly and a quick onset of action can be achieved. Medicament forms of this kind are suitable, in particular, for administering such active substances that are poorly absorbed by the gastrointestinal tract and/or exhibit a short plasma half-life.

The best known mucoadhesive administration forms are tablets which are configured in two layers and consist of a mucoadhesive layer and a retarding backing layer (AFTAB®, Rottapharm). There have been endeavours to improve the functional capability of such mucoadhesive tablets, for example by providing drainage notches which enable saliva liquid to be transported away from the application site. Such tablet systems are indeed capable of fulfilling their function, but they are experienced as unpleasant to the patients since they are relatively thick, hard and inflexible, and thereby induce a marked foreign body sensation.

Apart from the above, mucoadhesive "disks" are known which can be formulated on the basis of lipophile, insoluble polymer matrices and hydrophile mucoadhesive polymers and, if required, surfactants. These disks usually have a thickness of approx. 1 mm and therefore cause an unpleasant foreign body-sensation in the mouth.

From U.S. Pat. No. 4,713,243 there are known mono- or multilayered mucoadhesive films whose mucoadhesive layer consists of hydroxypropyl cellulose, an ethylene oxide homopolymer, a water-insoluble polymer (e.g. ethyl cellulose, propyl cellulose, polyethylene, polypropylene) and a plasticizer. These administration forms are considered more pleasant by the patients, but their usefulness is highly restricted on account of the only short period of adhesion. This short duration of adhesion is due to the fact that the polymers employed are readily soluble in water, so that no appreciable retardation of adhesion does occur. To achieve that the mentioned mucoadhesive films adhere to the mucosa for a prolonged period of time, the content of water-insoluble polymer components (e.g. ethyl cellulose, propyl cellulose) in the formulation must be increased. However, as a consequence, the mucoadhesive systems thus produced have a greater thickness, which increases the foreign body sensation during the period of application. In addition, the greater thickness entails a decrease in the release of active substance since the diffusion paths become longer and the diffusion coefficients diminish.

It has also been proposed (U.S. Pat. No. 5,719,197) to improve the coherence of mucoadhesive systems by using clay as an additive. However, such clays must be regarded as disadvantageous because of their property of adsorbing certain active substances or of affecting the active substance stability by catalytic effects. Furthermore, the weight and thickness of the system is markedly increased by these additives.

The task underlying the present invention was thereby to provide mucoadhesive administration forms which do not have the above-mentioned disadvantages, in particular inducement of a foreign body sensation, insufficient active substance release and too short a duration of adhesion.

Furthermore, these mucoadhesive medicament forms are to enable a quick onset of action on the one hand and on the other hand, enable a continuous and controlled active substance delivery over a prolonged period of time.

SUMMARY OF THE INVENTION

This task is surprisingly solved by film-shaped, at least double-layered transmucosal therapeutic systems according to the present invention and the alternative embodiments of the present invention.

The inventive therapeutic systems which are suitable, in particular, for transmucosal administration of active substances have a structure of at least two layers which are connected with each other. At least one of these layers contains active substance. One of the two sides of the inventive system is limited by a mucoadhesive layer which optionally contains active substance or is free of active substance. During application, this mucoadhesive layer is in contact with the absorbing mucosa, e.g. oral mucosa. The mucoadhesive layer of the system is connected with a backing layer which is mono-layered or double-layered and which may serve as an active substance reservoir. A special property of the mucoadhesive layer consists in the fact that it is capable of swelling in aqueous media, but is insoluble or only poorly, i.e. slowly, soluble therein. The insolubility or reduced solubility increases the period of adhesion to the mucosa, thereby enabling an active substance release that lasts for a prolonged period of time. Since the inventive systems are film-shaped and may have a thickness of less than 1 mm, they do not cause a foreign body sensation and are not unpleasant to the patients. Therefore, the acceptance of such medicament forms is improved.

DETAILED DESCRIPTION OF THE INVENTION
DETAILED DESCRIPTION OF THE INVENTION

It should be appreciated that the term "aqueous media" means, in addition to water, physiological liquids, such as saliva.

Figure 1:
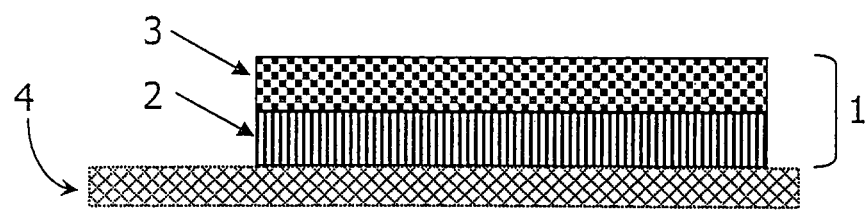
FIG. 1 is a schematic cross-section view of the structure of layers of a first embodiment of the mucoadhesive system according to the present invention.

Referring to FIG. 1 a system 1 is provided as a double-layered structure comprising a mucoadhesive layer or adhesive layer 2 and a backing layer or reservoir layer 3 connected to said mucoadhesive layer or adhesive layer 2. Mucoadhesive layer 2 of system 1 is in adhesive contact with a mucosa 4; status during application.

Figure 2:
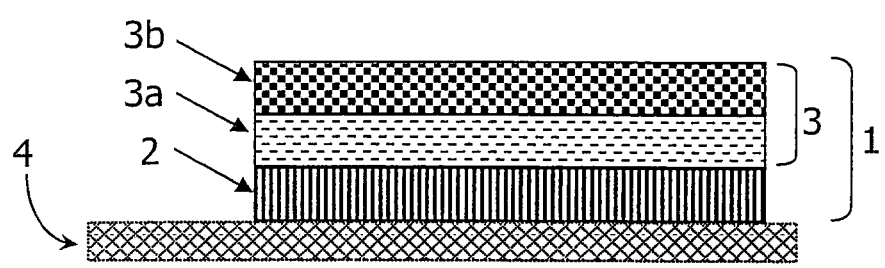
FIG. 2 is a schematic cross-section view of the structure of layers of a second embodiment of the mucoadhesive system according to the present invention.

Turning now to FIG. 2, system 1 is provided as a three-layered structure comprising a mucoadhesive layer 2 and a backing layer 3. Backing layer 3 consists of two individual reservoir layers 3a, 3b. Reservoir layer 3a is a middle layer 3a and reservoir layer 3b is an outer layer or boundary layer 3b. The reservoir layer 3b, closing the system towards the outside, is configured so as to be diffusion-controlled.

The mucoadhesive layer 2 consists mainly of a polymer mixture which is film-forming, swellable in aqueous media but non-soluble or only poorly soluble therein. The polymer mixture comprises at least one hydrophile, mucoadhesive polymer embedded or dispersed in a polymer matrix. Optionally, the mucoadhesive layer 2 may contain active substance(s) or additives.

The aforementioned hydrophile polymer, respectively the hydrophile polymers is/are selected from the group comprising hydrophile adhesive polymers carrying carboxyl groups, polyacrylates or polyacrylic acid derivatives (e.g. CARBOPOL® types, from the firm of B.F. Goodrich) and their salts, carboxymethyl cellulose and its salts, poly(methyl vinyl ether maleic anhydride) and its aqueous or alcoholic hydrolysates and salts (e.g. GANTREZ® types, such as GANTREZ-AN, -S, -ES, -MS; from ISP).

The above-mentioned polymer matrix of the mucoadhesive layer is essentially based on polymers which are hydrophilic, but insoluble or slowly soluble in an aqueous media. This polymer or these polymers is/are selected from the group of polyvinyl alcohols and polyacrylates. Other polymers known to those skilled in the art which enable an anchorage of the mucoadhesive layer 2 on the adjacent backing layer 3 that is durable in dry condition or in aqueous environment, may also be utilized.

To ensure a durable connection between the mucoadhesive layer 2 and the backing layer 3 superimposed thereon (respectively one of the individual layers 3a, 3b of the backing layer 3, in the case of a multi-layered backing layer) it is advantageous to select base polymers which are identical with those polymers employed for preparing the backing layer 3, or are at least chemically allied thereto.

Neighbouring layers of the film-shaped system contain one or more identical or chemically allied base polymers which are selected from the group of the polyacrylates.

In this way it can be ensured that for the period of application the mucoadhesive layer 2 remains durably connected with the backing layer 3, even in aqueous environment (oral cavity).

According to one embodiment of the present invention, the polymers of the mucoadhesive layer 2 are crosslinked by employing physical or/and chemical methods. By cross-linking, the degree of solubility can be reduced without affecting hydrophilicity. In this way it is possible to additionally, and with particular advantage, further improve the duration of adhesion to the mucosa 4. Suitable crosslinking reagents and crosslinking processes are known to those skilled in the art (e.g. use of aluminium acetylacetonate or titanyl acetylacetonate as crosslinking agent).

The mucoadhesive layer 2 may contain additives suitable for modulating the adhesive properties. It should be appreciated that these are known to those skilled in the art.

The backing layer 3 or (in the case of a multilayer backing layer) the individual layers 3a, 3b of the backing layer 3 is/are produced on the basis of polyacrylates, especially on the basis of neutralised polymethyl methacrylates (e.g. EUDRAGIT® E 100, EUDRAGIT® NE 30 D, PLASTOID® B; Röhm Pharma).—For example, polyacrylates which are capable of swelling in aqueous media—largely independently of the pH value—, but are not soluble therein may be employed. The backing layer 3 or at least one of the layers 3a, 3b forming the backing layer 3 may optionally contain one or more auxiliary substances, for example selected from the group of the plasticizers, penetration enhancers, solubilizers, colorants, pigments and matrix formers. It should be appreciated that suitable substances are known to those skilled in the art.

Suitable as plasticizers are, for instance, plasticizers from the group comprising hydrocarbons, alcohols (especially higher alcohols such as dodecanol, undecanol, octanol), polyhydric alcohols, polyethylene glycols, triglycerides, carboxylic acids, derivatives of carboxylic acids, ethers, esters (e.g. diethyl phthalate, n-butyl adipate, citric acid esters) and amines.

Suitable as absorption or permeation enhancers are, in particular, substances selected from the group comprising the following substances and substance classes: saturated or unsaturated fatty acids, fatty acid esters, especially esters with methanol, ethanol or isopropanol (e.g. oleic acid ethyl ester, oleic acid methyl ester, lauric acid methyl ester, lauric acid ethyl ester, adipic acid methyl ester, adipic acid ethyl ester), straight-chain or branched fatty alcohols and esters thereof, especially esters with acetic acid or lactic acid (e.g. ethyl oleate, ethyl laurate, ethyl palmitate, ethyl lactate, propyl lactate, propyl palmitate, propyl laurate, propyl oleate), polyhydric aliphatic alcohols or polyethylene glycols, sorbitan fatty acid esters and their derivatives obtained by ethoxylation, fatty alcohol ethoxylates, polyoxyethylene fatty acid ester; lauric acid diethanolamide, oleic acid diethanolamide, coconut fatty acid diethanolamide, D-alpha-tocopherol, lauric acid hexyl ester, 2-octyldodecanol, dexpanthenol, isopropylidene glycerol, transcutol (=diethylene glycol monoethyl ether), DEET (=N,N-diethyl-m-tolueneamide), solketal, ethanol, 1,2-propanediol or other short-chain alcohols (e.g. alcohols with up to 6 C atoms), as well as menthol and other essential oils or components of essential oils. To optimize active substance flow, it is also possible to use combinations of two or more enhancers.

The total constituent amount of plasticizers and permeation-enhancing substances may be up to 10%-wt, relative to the film-shaped medicament form. Having a content of less than 5%-wt., especially less than 1%-wt. may also be employed.

Examples for solubilizers are polyhydric alcohols such as 1,2-propanediol, butanediol, glycerol, polyethylene glycol 400, tetrahydrofurfuryl alcohol, diethylene glycol monoethyl ether, diethyl toluamide and monoisopropylidene glycerol. The portion of the solubilizers(s), relative to a medicament form, can be between 0.1 and 10%-wt, or even 0.5 to 5%-wt.

Suitable as pigments are, in particular, talcum, titanium dioxide, iron oxide or lamellar pigments. The pigment portion can amount to up to 80, or even up to 70%-wt, relative to the polymer portion in the respective layer.

As shown in FIG. 1, the inventive film-shaped mucoadhesive systems are constructed, in the simplest case, of two layers, namely a mucoadhesive layer 2 and a backing layer 3 connected to said backing layer 3. Backing layer 3 may serve as an active substance reservoir. In addition, the mucoadhesive layer 2 may also contain active substance, such as the same active substance as contained in the backing layer 3.

The active substance release from the system 1 to the mucosa 4 takes places by diffusion from the layers of the system 1.

According to one embodiment of the present invention, the backing layer 3 is modified by suitable additives in such a manner that the permeation of water and the diffusion of active substance in backing layer 3 is reduced or blocked, relative to the diffusion and permeation in the mucoadhesive layer 2.

In further embodiments of the invention, the systems may be designed as multilayer systems and can contain up to 6 individual layers, such as with a layer number of 2 to 4. In each case, one of the surfaces of the system is formed by a mucoadhesive layer 2. All of the layers may contain the same active substance, at the same or different concentrations.

The multilayered structure enables the manufacture of inventive systems which immediately after application release an initial burst dose and subsequently release a maintenance dose at a reduced delivery rate over a prolonged period of time (several hours, preferably 0.5 to 24 hours).

Especially advantageous are embodiments wherein the backing layer 3 is constructed of two or more individual layers 3a, 3b which are superimposed one upon another and are connected with one another. In this way it is possible to increase the active substance dose contained in the system 1. In addition, the individual layers may contain additives which modify the solubility and the diffusion coefficient of the active substance in the respective layer. Thereby, a multilayer is obtained which has a defined concentration gradient. This embodiment is particularly advantageous. The formation of a concentration gradient can, in addition, be assisted by providing the active substance in the individual layers in increasing or decreasing amounts or concentrations.

According to an additional embodiment of the present invention, it is provided that the backing layer 3 or that outer layer which is located on the side of the system that is opposite the mucoadhesive layer 2 and forms the outer surface, is modified by suitable additives such that the permeation of water and the diffusion of active substance in this layer is reduced or blocked, relative to the diffusion and permeation in the mucoadhesive layer 2 or in the other layers of the backing layer 3.

In this manner, a transmucosal system 1 is obtained which has a structure of at least three layers, namely comprising a mucoadhesive layer 2, at least one middle reservoir layer 3a connected to said mucoadhesive layer 2, and an outer layer or boundary layer 3b connected to said reservoir layer 2 (FIG. 2). In the latter layer, the diffusion of active substance—relative to the middle layer(s)—is reduced or even completely blocked.

The modification of the diffusion and permeation properties can be brought about, in particular, by varying the pigment content or/and by admixing suitable diffusion-retarding polymeric (e.g. ethyl cellulose, propyl cellulose) or non-polymeric auxiliary substances. In this manner, it is possible to adjust the diffusion properties of the backing layer 3, respectively the outermost layer 3b of the backing layer 3, between two extremes, namely between complete blockage of the diffusion on the one hand, and practically unimpeded or unmodified active substance diffusion from the matrix. Thus it is possible to optionally manufacture systems which release the active substance(s) on one side (i.e. only on the mucoadhesive side) or on two sides (i.e. on the mucoadhesive side and on that side of the system which is opposite thereto).

At least the middle layer(s) 3a of the system contain(s) the active substance. Outer boundary layer 3b may contain the same active substance(s). In addition, the mucoadhesive layer 2 may also contain an active substance.

With the above described, at least three-layered structure comprising the outer layer 3b, a system 1 is obtained wherein the delivery of active substance is controlled by a combination of matrix-controlled diffusion and membrane-controlled release.

Generally such a system, which is based on a mixed control (combination of matrix and membrane control) would release the active substance in a kind of saturation function, i.e. the delivery rate of the system would decrease further and further as the exhaustion of the system increases. By a suitable formulation, especially by a suitable selection of the matrix polymer(s) (increasing the portion of hydrophile functional groups), or by adding suitable hydrophile, water-binding additives (especially polyalcohols or polymeric surfactants with high HLB value, such as HLB$\geq$10, or even HLB$\geq$15), it is possible to influence and increase the degree of water uptake or the degree of swelling of the reservoir layer with increasing retention time of the system in the moist medium (i.e. at the application site in the oral cavity).

By the above-described measures, the diffusion coefficient in the reservoir layer 3 can be increased by an increase in the swelling or by an increase in the degree of hydration. It is thereby possible to compensate the decrease in the release rate, caused by the decrease of the concentration gradient, by an increase in the swelling and hydration of the active substance matrix such that a release results which is essentially linear, this is accompanied by a high exhaustion of the system.

These properties of the systems according to the invention are of significance especially with a view to a prolonged application of the system, for instance over a period of several hours (e.g. 2 to 24 h). This is true, in particular, where the substances to be administered have a correspondingly narrow therapeutic window.

At least one of the layers of the inventive film-shaped systems 1 contains an active substance or a combination of active substances. The polymers of the individual layers form a polymer matrix which may serve as an active substance reservoir. In this polymer matrix the active substance(s) are already contained, in dissolved, suspended or emulsified form, whereby "dissolved" is in the sense of a "solid solution". Suitable as active substances are, in particular, medicinal substances, such as highly efficacious medicinal substances, e.g. from the following groups: agents acting on the nervous system, psychopharmacological agents, sedatives, narcotics, hormones, insulin-like active agents, analgesics, anticonvulsives, anti-parkinson agents, medicaments acting on the cardiovascular system, anti-infectives, active agents for treating metabolic disturbances (e.g. lipid-lowering agents), agents acting on the muscular system, and others.

The inventive systems are suitable above all for administering medicaments that are subject to rapid metabolism or/and are absorbed only insufficiently via the gastrointestinal route.

The invention is further explained in the following examples.

Example

Preparation of a Three-Layered System (as in FIG. 2)

An active substance is dissolved in a neutral polyacrylate (e.g. EUDRAGIT® NE 30 D; Röhm), either directly or employing a suitable solvent known to those skilled in the art, if need be by using a dissolving intermediary or solubilizer.

The selection of the suitable method is dependent on the solubility, respectively the dissolving properties of the active agent employed.

Furthermore, an appropriate pigment is added to the active substance-containing polymer solution, e.g. talcum, $TiO_2$, iron oxide or lamellar pigments, and a homogeneous liquid is prepared. The pigment content is relatively high and is at approx. 60%-wt, relative to the polymer portion.

Subsequently, the viscosity of the liquid is adjusted such that it is suitable for the subsequent processing steps. The liquid is applied by a casting method or spraying method to an inert support and is subjected to subsequent drying which results in a thin film. The inert support employed must be such that the film remains adhering thereto after drying, but can be detached from the support without being destroyed.

In the same manner as above-described, a second liquid is prepared which differs from the first formulation only in that it does not contain the pigment or contains a lower portion of pigment. Thereby, the active substance content is increased relative to the entire solids content, as compared to the liquid prepared first. The second liquid is coated, again by means of a spraying or casting method, onto the layer prepared first and is subsequently dried so that a two-layer laminate with two reservoir layers is obtained.

To prepare the mucoadhesive layer, an aqueous solution of highly hydrolyzed polyvinyl alcohol (e.g. MOWIOL® 28-99, Clariant) of suitable concentration (e.g. 10%-wt.; optionally 0.5 to 60%-wt) is prepared, and a suitable portion of adhesive polymer (e.g. GANTREZ® S 95; ISP) is dissolved therein. The portion of adhesive polymer in this example corresponds to the polyvinyl alcohol portion (that is, mixing ratio 1:1; weight content). But other mixing ratios can be employed as well, e.g. in the range of 50:1 to 1:50, relative to the portion of adhesive:the portion of polyvinyl alcohol).

The resultant homogenous solution is coated, again employing a suitable application method, onto the previously prepared two-layer laminate, and subsequently dried.

This yields a three-layer laminate which—depending on the coating weight—is approx. 50 to 250 µm in thickness. The top side of this laminate has good tackiness in moist state and has mucoadhesive properties. The laminate as a whole has very good flexibility and adheres to a mucosa for several hours after application thereof.

The inventive transmucosal systems are advantageously suitable for administering active agents, especially medicaments, for therapeutic or prophylactic treatment in human or veterinary medicine.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A film-shaped therapeutic system comprising at least three layers connected with each other for transmucosal administration of active substances, wherein said at least three layers include:
   a mucoadhesive layer which is mucoadhesive in an aqueous environment; and
   a backing layer comprising at least one neutralized poly-methyl methacrylate and containing an active substance and a pigment, wherein said backing layer is at least two-layered and comprises a middle layer disposed upon said mucoadhesive layer and an outer layer, wherein one of said layers of said at least two-layered backing layer does not contain said pigment or contains a lower portion of said pigment than is contained in the respective other layer or layers of said at least two-layered backing layer;
   wherein said mucoadhesive layer swells in an aqueous medium but is insoluble or poorly soluble in the aqueous medium and contains a polymer mixture comprising at least one hydrophilic mucoadhesive polymer embedded or dispersed in a matrix comprising at least one polyvinyl alcohol, said mucoadhesive polymer being poly(methyl vinyl ether maleic anhydride);
   wherein said pigment is provided in an amount in the range of 60 wt.-80 wt. % relative to the polymer portion in the respective layer of the at least two-layered backing layer; and
   wherein the weight ratio of said mucoadhesive polymer to said polyvinyl alcohol is in the range of 50:1 to 1:50.

2. The film-shaped therapeutic system according to claim 1, wherein one of the layers of said at least two-layered backing layer contains a lower portion of said pigment than is contained in the respective other layer of said at least two-layered backing layer.

3. The film-shaped therapeutic system according to claim 1, wherein said mucoadhesive layer contains at least one active substance.

4. The film-shaped therapeutic system according to claim 1, wherein said mucoadhesive layer further contains at least one mucoadhesive polymer selected from the group consisting of polyacrylates and salts of polyacrylates.

5. The film-shaped therapeutic system according to claim 1, wherein said mucoadhesive layer further contains at least one mucoadhesive polymer selected from the group consisting of carboxymethyl cellulose and salts of carboxymethyl cellulose.

6. The film-shaped therapeutic system according to claim 1, wherein said mucoadhesive layer further contains at least one mucoadhesive polymer selected from the group consisting of carboxyl groups-carrying hydrophilic adhesive polymers.

7. The film-shaped therapeutic system according to claim 1, wherein said mucoadhesive layer further contains at least one mucoadhesive polymer selected from the group consisting of polymers of acrylic acid crosslinked with allyl sucrose or allyl pentaerythritol.

8. The film-shaped therapeutic system according to claim 1, wherein the polymers of the mucoadhesive layer are crosslinked by physical or chemical methods.

9. The film-shaped therapeutic system according to claim 1, wherein said system comprises four to six layers.

10. The film-shaped therapeutic system according to claim 1, wherein at least two layers contain the same active substance at different concentrations such that a concentration gradient is formed.

11. The film-shaped therapeutic system according to claim 1, wherein said pigment is selected from the group consisting of talcum, $TiO_2$, iron oxide and lamellar pigments.

12. The film-shaped therapeutic system according to claim 1, wherein the system is a three-layered laminate having a thickness of 50 to 250 µm.

13. The film-shaped therapeutic system according to claim 1, wherein two adjacent layers of said at least two-layered backing layer which are in contact with each other contain polymers selected from the group consisting of polyacrylates.

14. The film-shaped therapeutic system according to claim 1, wherein said middle layer disposed upon said mucoadhesive layer contains said active substance.

15. The film-shaped therapeutic system according to claim 1, wherein said middle layer disposed upon said mucoadhesive layer and said outer layer contain said active substance.

16. The film-shaped therapeutic system according to claim 1, wherein the weight ratio of said mucoadhesive polymer and said polyvinyl alcohol is 1:1.

17. The film-shaped therapeutic system according to claim 1, wherein said outer layer of said at least two-layered backing layer further contains polymeric auxiliary substances selected from the group consisting of ethyl cellulose and propyl cellulose.

18. The film-shaped therapeutic system according to claim 1, wherein said backing layer contains at least one of the following selected from the group consisting of at least one plasticizer, at least one penetration enhancer/permeation enhancing substance and at least one solubilizer.

19. The film-shaped therapeutic system according to claim 1, wherein the backing layer forms a boundary layer wherein the permeation of water and the diffusion of active substance is reduced in the boundary layer relative to the other layers of said film-shaped therapeutic system.

20. The film-shaped therapeutic system according to claim 1, wherein the outermost layer of said at least two-layered backing layer relative to said mucoadhesive layer forms a boundary layer wherein the permeation of water and the diffusion of active substance in the boundary layer is reduced relative to the other layers of said film-shaped therapeutic system.

21. The film-shaped therapeutic system according to claim 1, wherein said film-shaped therapeutic system comprises at least three layers, comprising said mucoadhesive layer, at least one middle layer, and an outermost backing layer, wherein said at least one middle layer is a middle reservoir layer, wherein said outermost backing layer forms a boundary layer for reducing the permeation of water and diffusion of active substance relative to the other layers of said film-shaped therapeutic system.

22. The film-shaped therapeutic system according to claim 21, wherein said outermost backing layer is a boundary layer and contains additives for reducing or blocking the diffusion of the active substance, the additives being selected from the group consisting of pigments and diffusion-retarding polymers.

23. The film-shaped therapeutic system according to claim 21, wherein said at least one middle reservoir layer contains at least one additive for increasing the swelling capacity and the hydration of the reservoir matrix, wherein said additives are hydrophilic water-binding substances.

24. The film-shaped therapeutic system according to claim 23, wherein said hydrophilic water-binding substances are selected from the group consisting of poly-alcohols and polymeric surfactants with an HLB value of greater than or equal to 10.

25. The film-shaped therapeutic system according to claim 1, wherein the active substances are present in a form selected from the group consisting of dissolved, suspended and emulsified.

26. The film-shaped therapeutic system according to claim 1, wherein the at least three layers comprise additives for modifying the solubility and the diffusion coefficient of the active substance in the respective layer.

27. The film-shaped therapeutic system according to claim 1, wherein said pigment is provided in an amount in the range of 60 wt. %-70 wt. % relative to the polymer portion in the respective layer.

28. The film-shaped therapeutic system according to claim 18, wherein the total constituent amount of said at least one plasticizer and said at least one penetration enhancer/permeation enhancing substance is up to 10 wt. % relative to the film-shaped therapeutic system.

29. The film-shaped therapeutic system according to claim 28, wherein the total constituent amount of said at least one plasticizer and said at least one penetration enhancer/permeation enhancing substance is less than 5 wt. % relative to the film-shaped therapeutic system.

30. The film-shaped therapeutic system according to claim 29, wherein the total constituent amount of said at least one plasticizer and said at least one penetration enhancer/permeation enhancing substance is less than 1 wt. % relative to the film-shaped therapeutic system.

31. The film-shaped therapeutic system according to claim 18, wherein said at least one plasticizer is at least one selected from the group consisting of hydrocarbons, alcohols, polyhydric alcohols, polyethylene glycols, triglycerides, carboxylic acids, ethers, esters and amines.

32. The film-shaped therapeutic system according to claim 31, wherein said alcohols are higher alcohols selected from the group consisting of dodecanol, undecanol and octanol, and wherein said esters are selected from the group consisting of diethyl phthalate esters, n-butyl adipate esters and citric acid esters.

33. The film-shaped therapeutic system according to claim 18, wherein said at least one penetration enhancer/permeation enhancing substance is at least one selected from the group consisting of saturated or unsaturated fatty acids, fatty acid esters, straight-chain or branched fatty alcohols and esters thereof, polyhydric aliphatic alcohols, polyethylene glycols, sorbitan fatty acid esters and their derivatives obtained by ethoxylation, fatty alcohol ethoxylates, polyoxyethylene fatty acid ester; lauric acid diethanolamide, oleic acid diethanolamide, coconut fatty acid diethanolamide, D-alpha-tocopherol, lauric acid hexyl ester, 2-octyldodecanol, dexpanthenol, isopropylidene glycerol, transcutol (diethylene glycol monoethyl ether), DEET (N,N-diethyl-m-tolueneamide), solketal, ethanol, 1,2-propanediol or other short-chain alcohols, menthol and other essential oils.

34. The film-shaped therapeutic system according to claim 33, wherein said fatty acid esters are selected from the group consisting of esters with methanol, ethanol or isopropanol, wherein said straight-chain or branched fatty alcohols and esters thereof are selected from the group consisting of esters with acetic acid or lactic acid, and wherein said 1,2-propanediol or other short-chain alcohols are selected from the group consisting of alcohols with up to six Carbon atoms.

35. The film-shaped therapeutic system according to claim 34, wherein said esters with methanol, ethanol or isopropanol are selected from the group consisting of oleic acid ethyl ester, oleic acid methyl ester, lauric acid methyl ester, lauric acid ethyl ester, adipic acid methyl ester, and adipic acid ethyl ester, and wherein said esters with acetic acid or lactic acid are selected from the group consisting of ethyl oleate, ethyl laurate, ethyl palmitate, ethyl lactate, propyl lactate, propyl palmitate, propyl laurate, and propyl oleate.

36. The film-shaped therapeutic system according to claim 18, wherein said at least one solubilizer is at least one polyhydric alcohol.

37. The film-shaped therapeutic system according to claim 36, wherein said at least one polyhydric alcohol is selected from the group consisting of 1,2-propanediol, butanediol, glycerol, polyethylene glycol 400, tetrahydrofurfuryl alcohol, diethylene glycol monoethyl ether, diethyl toluamide and monoisopropylidene glycerol.

38. The film-shaped therapeutic system according to claim 18, wherein the portion of said at least one solubilizer relative to the film-shaped therapeutic system is in the range of about 0.1 wt. %-10 wt. %.

39. The film-shaped therapeutic system according to claim 38, wherein the portion of said at least one solubilizer relative to the film-shaped therapeutic system is in the range of about between 0.5 wt. %-5 wt. %.

40. A three-layered film-shaped therapeutic system wherein each layer is connected with an adjacent layer for transmucosal administration of active substances, wherein at least one layer of said three-layered film-shaped therapeutic system comprises at least one active substance, and wherein said three-layered film-shaped therapeutic system comprises:
- a mucoadhesive layer which is mucoadhesive in an aqueous environment; and
- a two-layered backing layer, said two-layered backing layer comprising at least one neutralized polymethyl methacrylate and containing an active substance and a pigment, wherein said two-layered backing layer comprises a middle layer relative to said three-layered film-shaped therapeutic system being to disposed upon said mucoadhesive layer, and an outer layer disposed upon the layer that is disposed upon said mucoadhesive layer, wherein one of said layers of said two-layered backing layer does not contain said pigment or contains a lower portion of said pigment than is contained in the respective other layer of said two-layered backing layer;
- wherein said mucoadhesive layer swells in an aqueous medium but is insoluble or poorly soluble in the aqueous medium and contains a polymer mixture comprising at least one hydrophilic mucoadhesive polymer embedded or dispersed in a matrix comprising at least one polyvinyl alcohol, said mucoadhesive polymer being poly(methyl vinyl ether maleic anhydride);
- wherein said pigment is provided in one layer of said two-layered backing layer in an amount in the range of 60-80 wt. % relative to the polymer portion in the layer;
- wherein said pigment is provided in one layer of said two-layered backing layer in an amount less than that of the other layer of said two-layered backing layer; and
- wherein the weight ratio of said mucoadhesive polymer to said polyvinyl alcohol is in the range of 50:1 to 1:50.

41. The three-layered film-shaped therapeutic system according to claim 40, wherein said pigment provided in one layer of said two-layered backing layer is provided in an amount of 60 wt. % relative to the polymer portion in the layer.

* * * * *